(12) United States Patent
Bernstein et al.

(10) Patent No.: US 6,292,178 B1
(45) Date of Patent: Sep. 18, 2001

(54) SCREEN NAVIGATION CONTROL APPARATUS FOR OPHTHALMIC SURGICAL INSTRUMENTS

(75) Inventors: Alec Bernstein, Oxnard; Monika M. Zych, Woodland Hills; Laura H. Robin, Ventura, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/174,776

(22) Filed: Oct. 19, 1998

(51) Int. Cl.$^7$ .................................................. G09G 5/00
(52) U.S. Cl. ........................ 345/173; 604/22; 600/118; 434/323
(58) Field of Search .................... 345/173, 168; 434/262, 267, 323; 606/5, 4; 600/109, 131, 111, 118; 604/22, 66, 67

(56) References Cited

U.S. PATENT DOCUMENTS

| | | | |
|---|---|---|---|
| 4,264,849 | 4/1981 | Fleischer et al. | 318/568 |
| 4,933,843 | 6/1990 | Scheller et al. | 364/413.01 |
| 5,053,758 | 10/1991 | Cornett et al. | 340/712 |
| 5,098,426 | 3/1992 | Sklar et al. | 606/5 |
| 5,157,603 | 10/1992 | Scheller et al. | 364/413.01 |
| 5,455,766 | 10/1995 | Scheller et al. | 364/413.01 |
| 5,598,527 | * 1/1997 | Debrus et al. | 345/168 |
| 5,706,030 | * 1/1998 | Ishigami et al. | 345/168 |

FOREIGN PATENT DOCUMENTS

| | | | |
|---|---|---|---|
| 0 424 686 A1 | 5/1991 | (EP) | A61B/17/32 |
| 0 424 687 A1 | 5/1991 | (EP) | A61F/9/00 |
| WO 98/25556 | 6/1998 | (WO) | A61F/9/00 |

\* cited by examiner

Primary Examiner—Amare Mengistu
(74) Attorney, Agent, or Firm—Walter A. Hackler

(57) ABSTRACT

Screen navigation control apparatus for an ophthalmic surgical instrument, the apparatus includes a monitor having a screen and a monitor bezel having a generally horizontal shelf aligned with a bottom of said screen and a generally vertical portion aligned with a side of the screen. A plurality of spaced apart switches, disposed on the horizontal shelf, one provided for activating corresponding vertical displays on screen, each corresponding vertical display being aligned with one of the switch means. A sliding touch control panel, disposed in a continuous strip along the bezel vertical portion enables selection of functions and alphanumeric data appearing in an activated vertical display. A computer is utilized for generating vertical displays generally parallel to the sliding touch control means. The vertical displays include a main menu having as a first vertical display a mode menu offering a selection of diathemy, phaco, irrigation/aspiration or vitrectomy mode of operating the surgical instrument, a second vertical display offering a selection of program for saved preferences, a third vertical display offering a selection for diagnostics, fluidics and testing maintenance of the surgical instrument, and a fourth vertical display offering a selection for ending operation of the surgical instrument.

8 Claims, 12 Drawing Sheets

DR. GRINDSTONE
HARD CATARACT 2
PHACO

|  | MMP 1 | MMP 2 | MMP 3 | MMP 4 | MMP 5 |
|---|---|---|---|---|---|
| OCC MODE | ENABLED | DISABLED | ENABLED | ENABLED | ENABLED |
|  |  |  |  |  |  |
| VACUUM | PANEL | LINEAR | LINEAR | PANEL | LINEAR |
| MAX | 350 | 350 | 350 | 350 | 350 |
| THRESHOLD | 250 | 250 | 250 | 250 | 250 |
|  |  |  |  |  |  |
| ASPIRATION |  |  |  |  |  |
| OCCULUDED | LINEAR | PANEL | LINEAR | LINEAR | LINEAR |
| MAX | 250 | 250 | 250 | 250 | 250 |
| UNOCCLUDED | PANEL | — | PANEL | PANEL | PANEL |
| MAX | 120 | — | 120 | 120 | 120 |
|  |  |  |  |  |  |
| POWER |  |  |  |  |  |
| OCCLUDED | BURST | — | AUTOBURST | CONT. | PULSE |
| RATE | 230 | — | — | — | 130 |
| MAX | 25 | — | 250 | 25 | 25 |
| UNOCCLUDED | PULSE | BURST | CONT. | PULSE | CONT. |
| RATE | 30 | 175 |  | 175 | 175 |
| MAX | 250 | 30 | 300 | 30 | 30 |
|  |  |  |  |  |  |
| PERIPHALS |  |  |  |  |  |
| CONT. 1HR. | ON | ON | ON | ON | ON |
| BOTTLE HT | 75 | 75 | 75 | 75 | 75 |
|  |  |  |  |  |  |
| FOOTPEDAL |  |  |  |  |  |
| PEDAL PIVOT | FRONT | FRONT | FRONT | FRONT | FRONT |
| VIB. FEEDBACK | ON | OFF | ON | OFF | ON |
| VIB. SETTING | 90 |  | 90 |  | 90 |
| DEP. FORCE | 100 | 100 | 100 | 100 | 100 |
| SIDE SWITCH | ON | ON | ON | ON | ON |
| POS. THRES | 10 | 10 | 10 | 10 | 10 |

| MODE | ← | SELECT | → |
|---|---|---|---|

FIG. 12

SCREEN NAVIGATION CONTROL APPARATUS FOR OPHTHALMIC SURGICAL INSTRUMENTS

The present invention generally relates to ophthalmic surgical instruments and is particularly, directed to navigation control apparatus for operating such ophthalmic surgical instruments.

Many ophthalmic surgical instruments include handpieces for effecting a plurality of functions simultaneously, such as, for example, phacoemulsification, which includes fragmenting of lens tissue and simultaneously providing irrigation fluid and aspiration of fluids and fragmented eye tissue from the eye.

A control console is typically configured to coordinate fluid flow and pressure to the handpiece while at the same time also providing control of electrical power necessary for operating the handpiece.

Heretofore available control consoles have generally included numerous control features with an assortment of switch mechanisms and video screens for facilitating the coordination of the multiple settings required for a variety of surgical procedures which include vitrectomy, microscissor cutting, as well as fragmentation/emulsification of lens tissue.

A typical environment for ophthalmic surgical instruments is a suitable hospital or clinic in which the apparatus is utilized by a great number of surgeons.

This of course complicates and compounds the number of control configurations which the console must handle. For example, surgeons with various specialties and operating techniques each may desire or require different response characteristics which are of course programmable in the control console computer.

Thus, while modern control consoles provide a generally universal and programmable control system which can handle a variety of different surgical procedures and be specifically alterable to the response characteristics which any given surgeon may require, it should be appreciated that organization of the control system is quite complicated.

Navigating such control systems in an efficient manner can greatly reduce not only the set up time of the surgical apparatus and controls therefore, but also modifications of settings as my be desired during operating procedures.

Heretofore instruments have utilized various console push buttons and potentiometer knobs which are programmable, see for example, U.S. Pat. No. 4,933,843. While an electronic display screen on the console may be useful for displaying the transfunction of each programmable button or knob, the entry of information is still awkward when considering the great amount of input which must be selected or recalled from a computer memory.

The present invention provides screen navigation control apparatus and a method for the efficient utilization of ophthalmic surgical instruments.

SUMMARY OF THE INVENTION

Screen navigation control apparatus in accordance with the present invention for an ophthalmic surgical instrument generally includes a monitor having a screen along with a monitor bezel having a generally horizontal shelf aligned with a bottom of a screen and a generally vertical portion aligned with the side of the screen. Efficient operation may be provided when the screen is oriented in a "Landscape" position.

A sliding touch switch disposed on the bezel vertical portion provide a means for activating corresponding vertical displays on the screen.

A plurality of spaced apart switches may be disposed along the bezel shelf for selecting functions and alphanumeric data appearing in an activated vertical display.

Importantly the switches in the bezel shelf and the sliding switch disposed in the bezel vertical portion, and the adjoining monitor screen offer an operating relationship which provides a system for rapid review, editing and saving of information during surgery.

Means are provided for generating vertical displays which are generally parallel to the sliding touch control means in the bezel vertical position with the vertical displays including a main menu having as a first vertical display a mode menu offering a selection of diathermy, phaco, irrigation/aspiration, or vitrectomy mode of operating a surgical instrument. A second vertical display offers a selection of programs saved preferences, such as specific information and settings for a plurality of doctors, different procedures which may be performed by the doctor, and specific settings desired by the doctor for providing a characteristic response the surgical instrument tailored to the doctor's desires.

A third vertical display offers a selection for diagnostics, fluidics and testing/maintenance of the surgical instrument and a fourth vertical display offers a selection for ending operation of the surgical instrument.

More particularly, the vertical displays may include upon selection of a phaco mode of operation, a first selection display for vacuum settings, a second selection display for aspiration settings and a third selection display for power settings.

When necessary for selecting values for input to a control computer the means for generating the vertical displays includes means for projecting a field of alphanumeric characters on the screen which are spaced apart from the vertical displays and adjacent to the vertical sliding touch control means and parallel therewith. A specific alphanumeric character is highlighted corresponding to a position of a user's finger on the sliding touch control means. The selection may occur by release of the user's finger from the sliding touch control means when the sliding touch control means provides for actuation upon release thereof.

More particularly in accordance with the present invention, at least one of the vertical displays may include a list of readable options and a box outline and the sliding touch control means is operative upon touching thereof to move the box outlined to surround one of the readable options with release of the sliding touch control means being effective to select the surrounded readable option and stabilize the box outlined therearound. Thus input to the control system is rapidly and effectively provided by the present system.

In addition, in accordance with the present invention at least one of the vertical displays includes an icon having a space therein for entry of a numerical value and the sliding touch control means is operative, upon touching thereof, to indicate possible numerical values for entry into the icon space upon moving of the user's finger along the sliding touch control means when in contact therewith. Release of the sliding touch control means by the user's finger is effective to display the last possible numerical value in the icon space.

BRIEF DESCRIPTION OF THE DRAWINGS

The present invention may be more readily understood by consideration of the following detailed description particularly in conjunction with the accompanying drawings in which:

FIGS. 2–12 are displays in accordance with the present invention which appear on the screen of the monitor shown in FIG. 1 and are aligned with and controlled by the horizontal switches and sliding touch control as will be hereinafter described in greater detail.

DETAILED DESCRIPTION OF THE DRAWINGS

Figure 1:
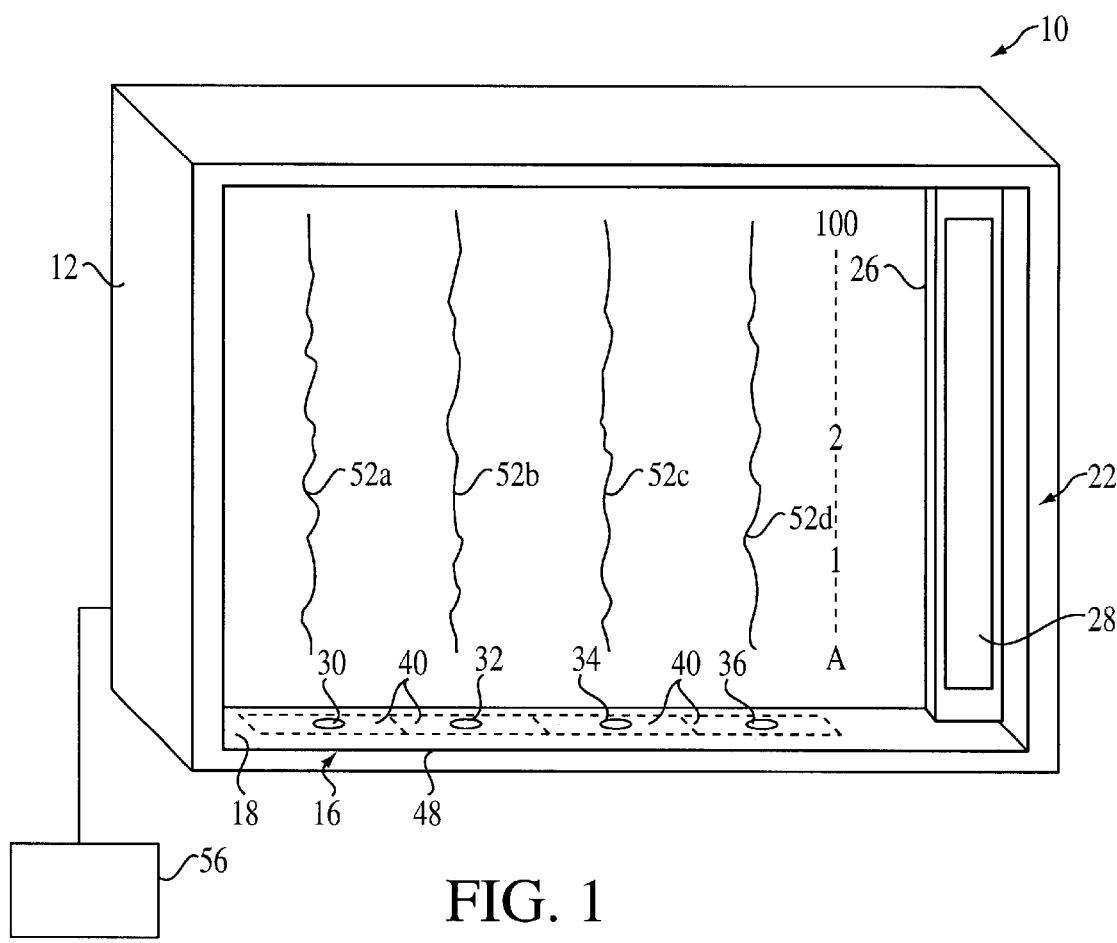
FIG. 1 is a perspective view of a monitor and screen, shown in a "Landscape" orientation, along with a monitor bezel incorporating a horizontal shelf with spaced apart switches therein a generally vertical portion with a touch sliding control therein.
Figure 2:
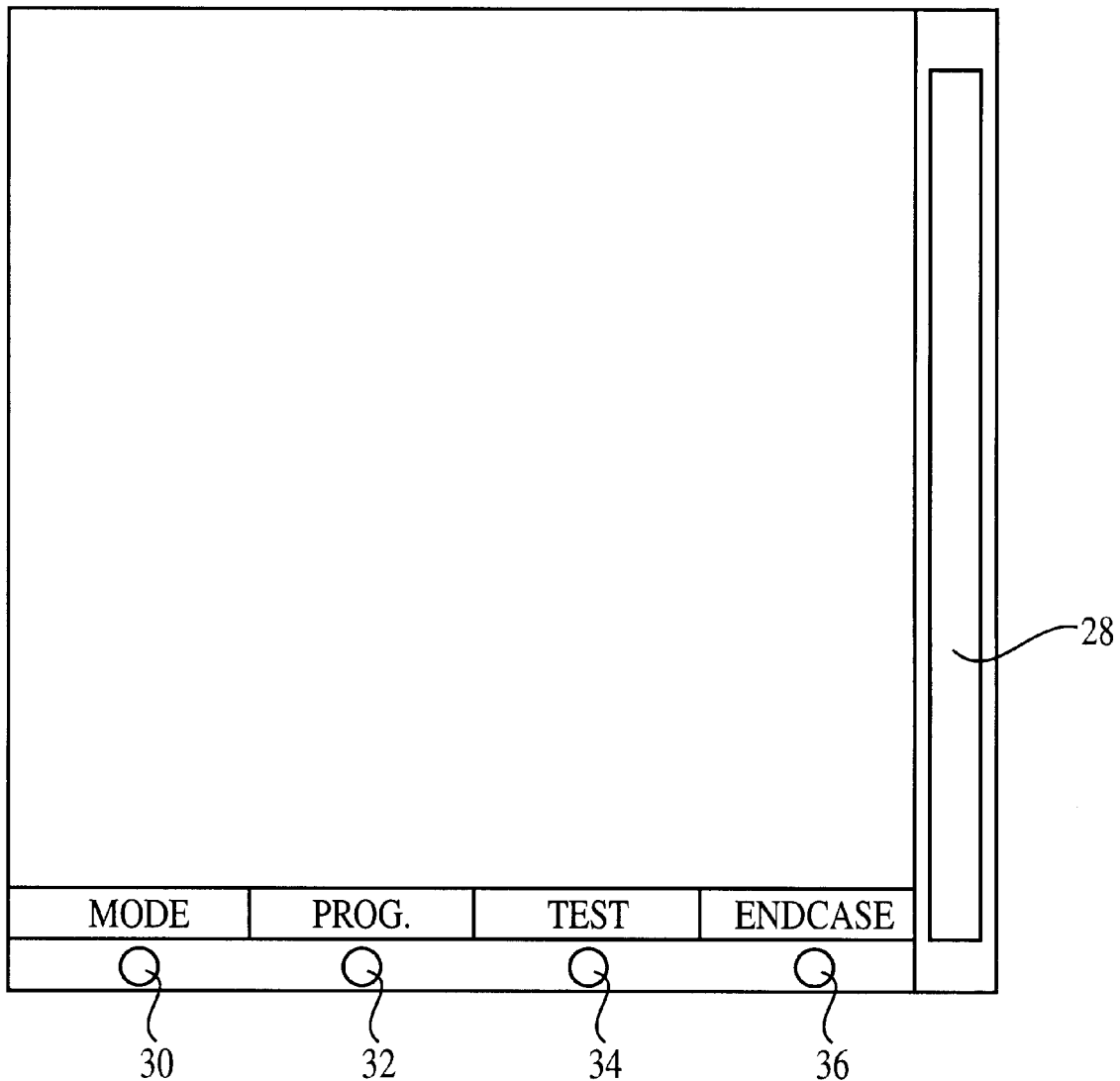

Turning now to FIG. 1 there is shown a screen navigation control apparatus 10 in accordance with the present invention which generally includes a monitor 12 having a screen 14 along with a monitor bezel 16 having a generally horizontal shelf 18 aligned with a bottom 20 of the screen 14 and a generally vertical portion 22 aligned with a side 26 of the screen 14.

A sliding touch control panel or strip 28, of conventional design, is disposed in a continuous manner along the vertical position 22 of the bezel 16 and provides a means for selecting functions and alphanumeric data appearing in an activated vertical display, the operation being hereinafter described in greater detail.

Disposed in the bezel horizontal shelf, or portion, 18 are a plurality of spaced apart button switches 30, 32, 34, 36 which provide a means for activating the corresponding vertical displays 52a, 52b, 52c, 52d, (also see FIGS. 2–12) on the screen 14 as will be hereinafter described in greater detail. Importantly, each of the vertical displays 52a, 52b, 52c, 52d, are aligned with one of the switches 30, 32, 34, 36. It should be appreciated that the switches 30, 32, 34, 36 may be replaced with sliding touch switches, or touch panels, 40 having designated areas (shown in broken line) corresponding to the switch buttons 30, 32, 34, 36.

A properly programmed computer 56 provides a means for generating the vertical displays 52a, 52b, 52c, 52d, as well as the vertical displays shown in FIGS. 2–12, the computer 56 being of any suitable type and programmed in a conventional manner for controlling a console for use with surgical instruments, not shown. For example, see the control system set forth in U.S. Pat. No. 4,933,843.

To select a mode or activate a menu, a user presses a button 30, 32, 34, 36 aligned with a mode or menu for activation. As diagrammed in FIG. 2, selection of mode is done by pressing button 30, selection of program is done by pressing button 32 and testing is formed by pushing button 34 and button 36 is selected for ending operation.

When the mode or menu becomes active by pressing the button 30, 32, 34, 36 a vertical display is shown and thereafter the slider 28 is used to select values within the active mode or menu, as hereinafter described. The unique configuration of the X/Y relationship and slider button switches enable the user to rapidly review, edit and save information used during phaco surgery. Thus, the screen navigation control apparatus 10 in accordance with the present invention represents a substantial improvement in surgical instrument control by way of its facilitation of data entry and access.

Figure 3:
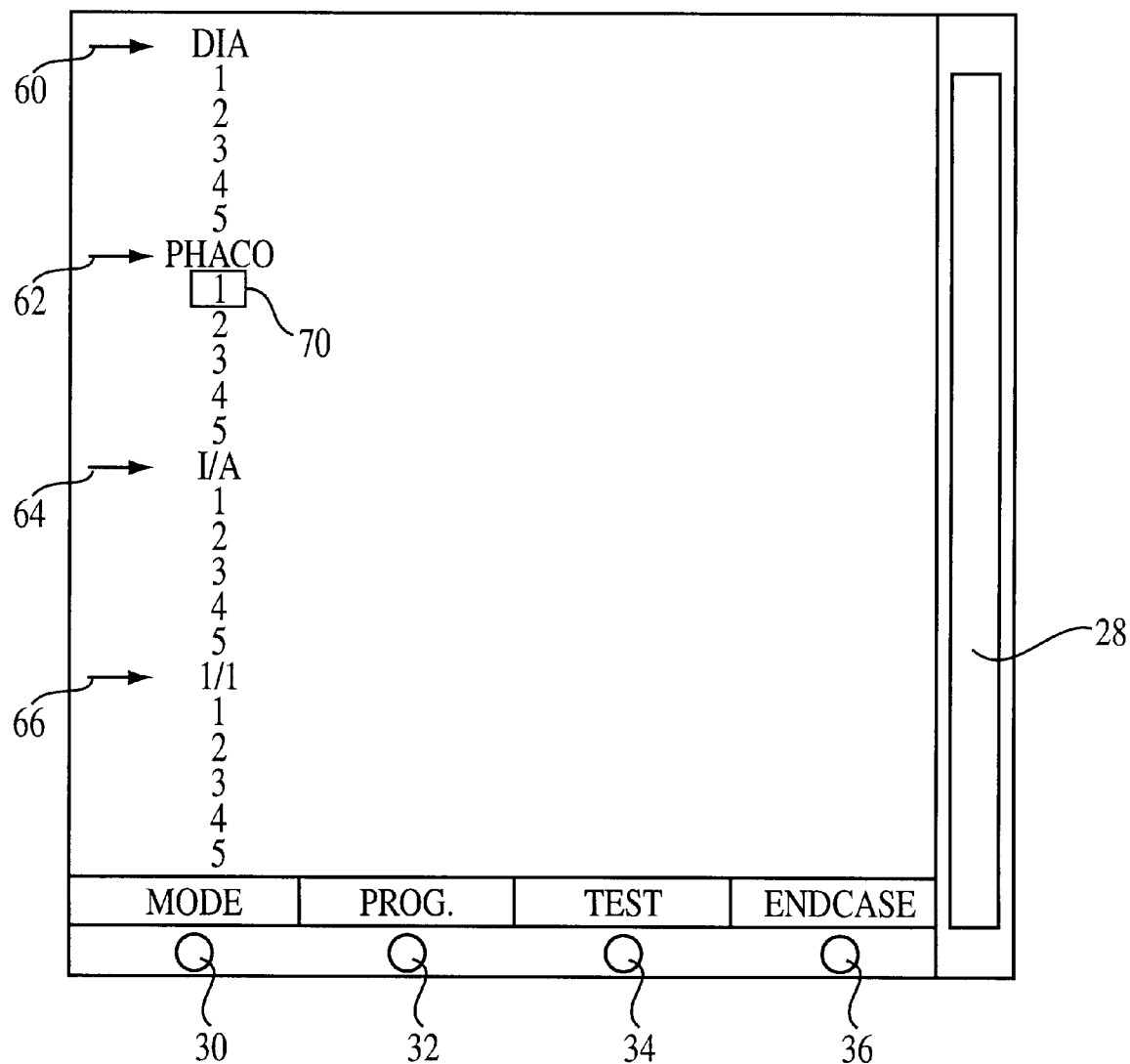

As shown in FIG. 3 when the mode is activated by button 30, the computer generates a vertical display corresponding thereto offering a selection of diathermy (see arrow 60), phaco operation (see arrow 62), irrigation/aspiration (see arrow 64) or victrectomy (see arrow 66).

A box outline 70 as shown in FIG. 3 surrounding a selected phaco procedure indicated as -1-which indicates a selected mode. It should be appreciated that while a box outline 70 is shown, any other graphic, means may be utilized, for example, underscraping, bold face or hi-lite graphics. The sliding touch control means 28 is operative upon touching thereof to move the box outline 70 to surround any one of the readable options with release of the sliding touch control means 28 being affected to select the surrounded readable option and stabilize the box outline 70 therearound. The selection is entered into the computer 56.

Figure 4:
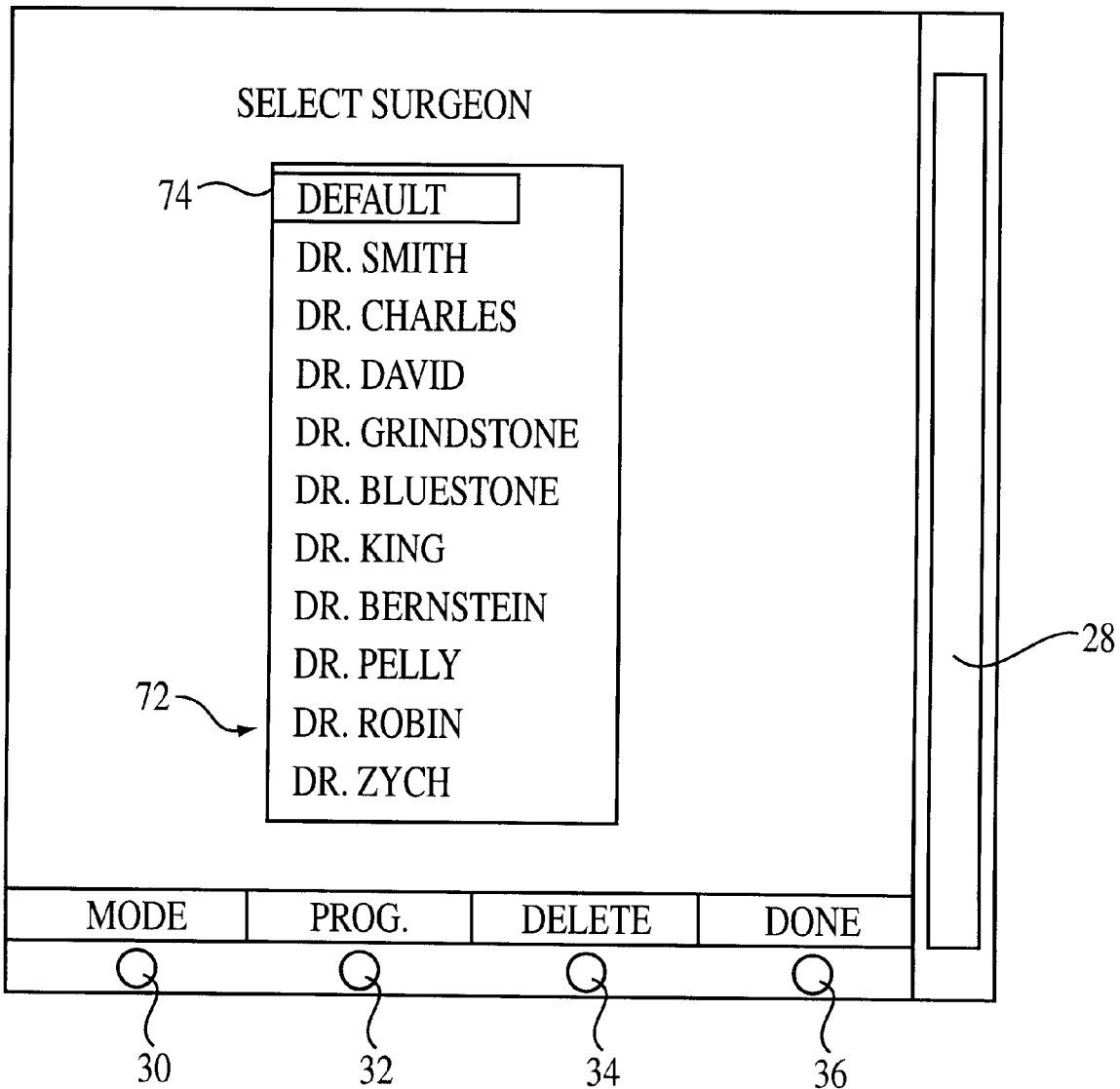
Figure 5:
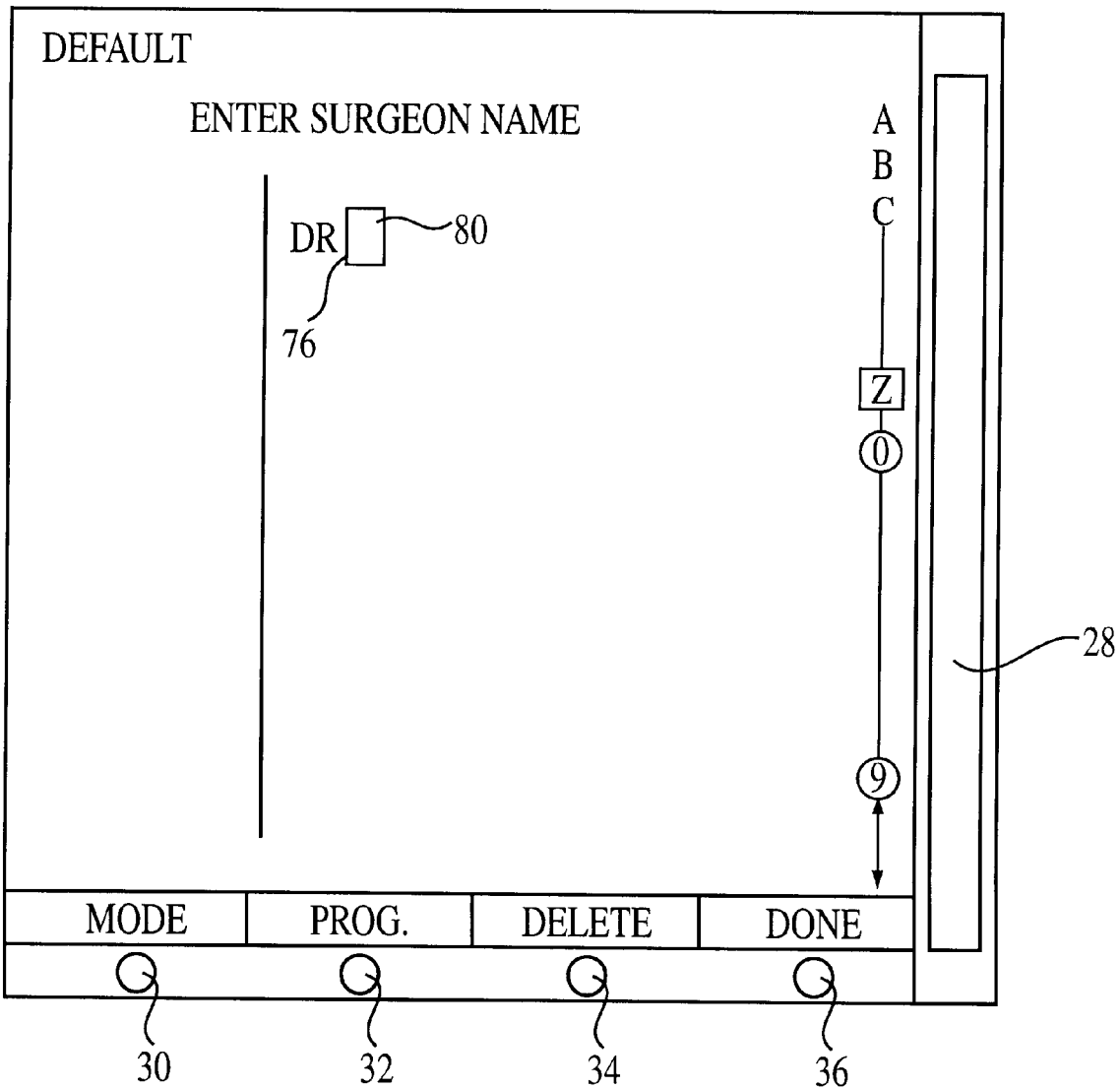
Figure 6:
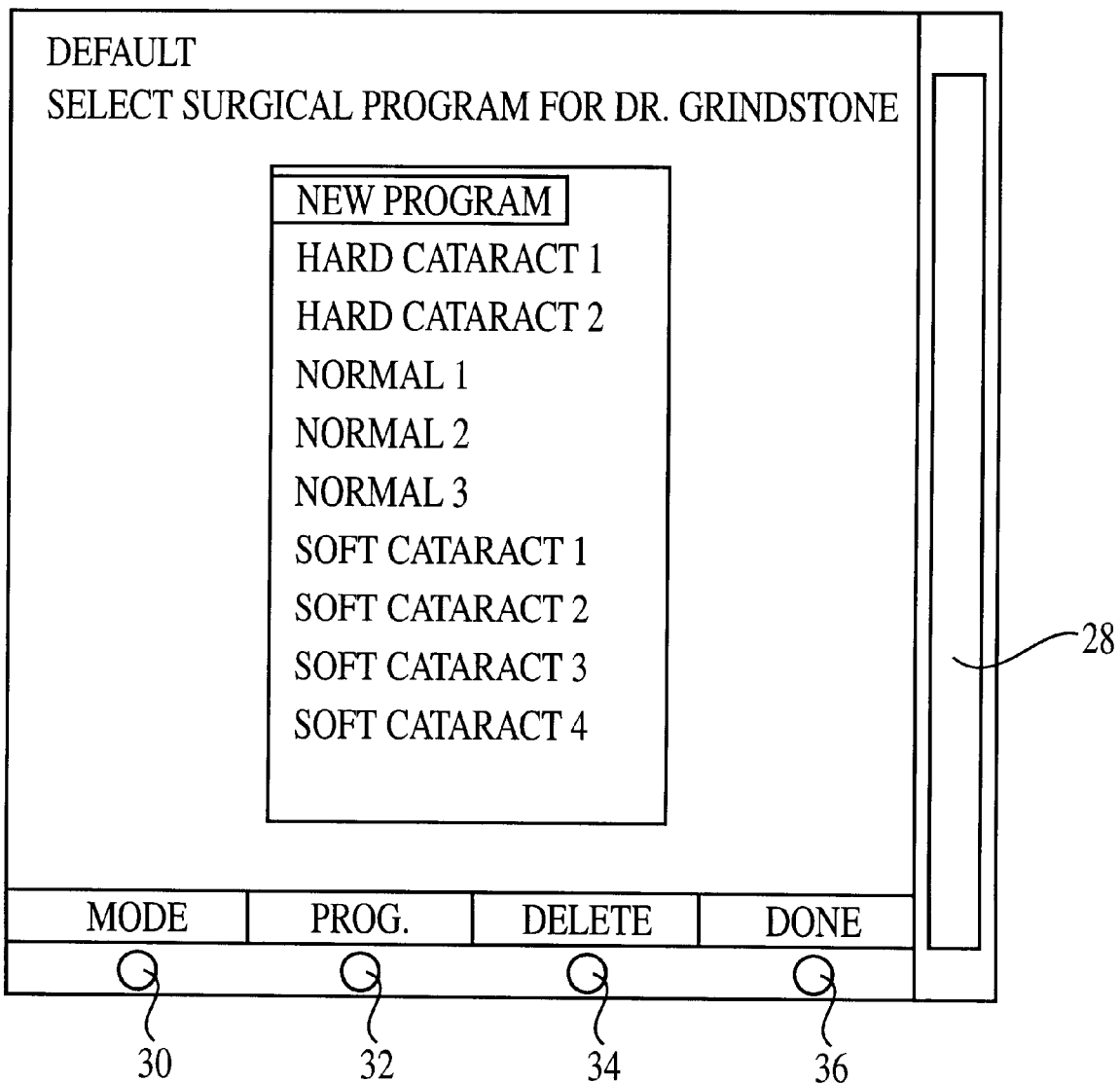
Figure 7:
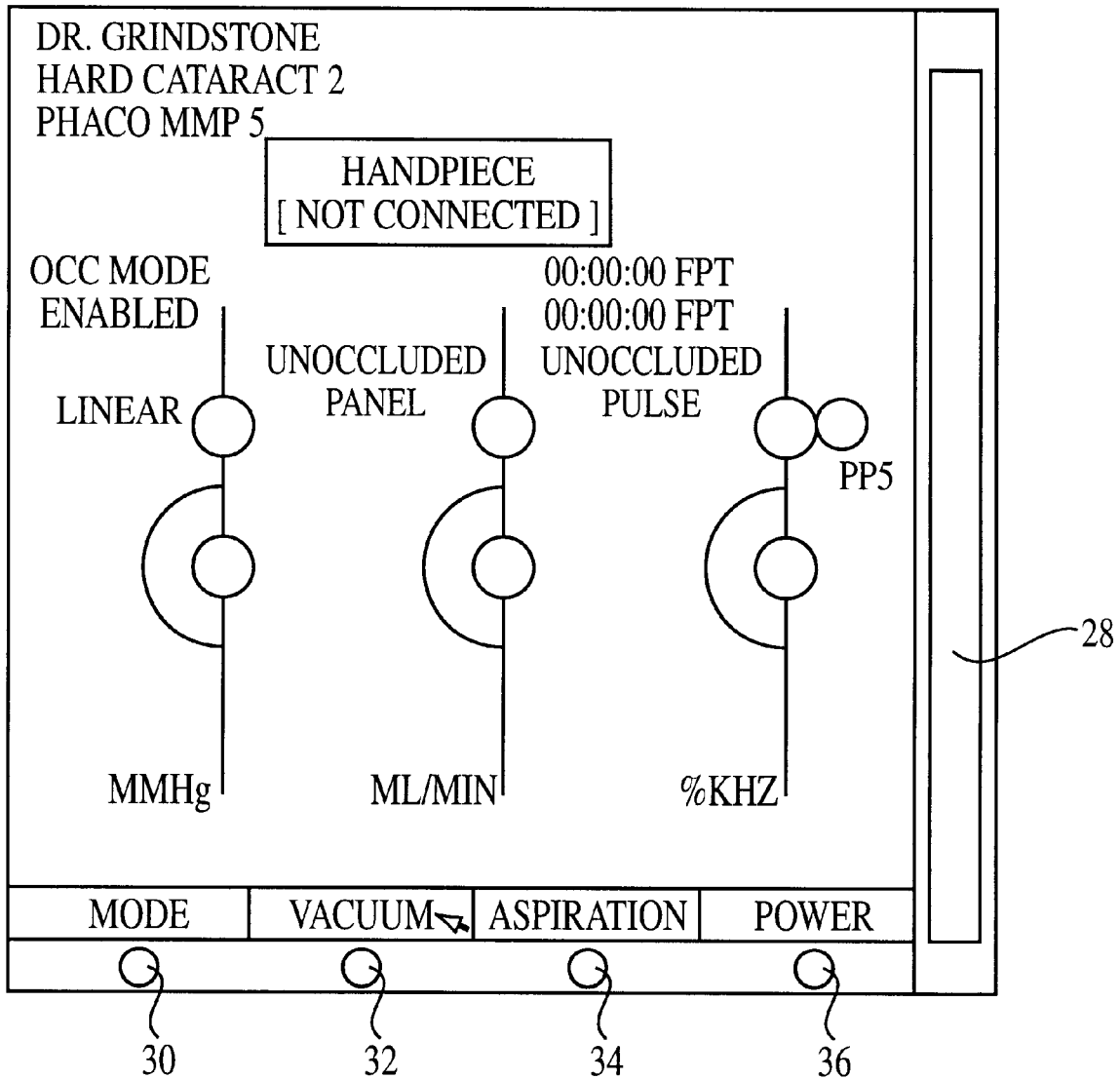
Figure 8:
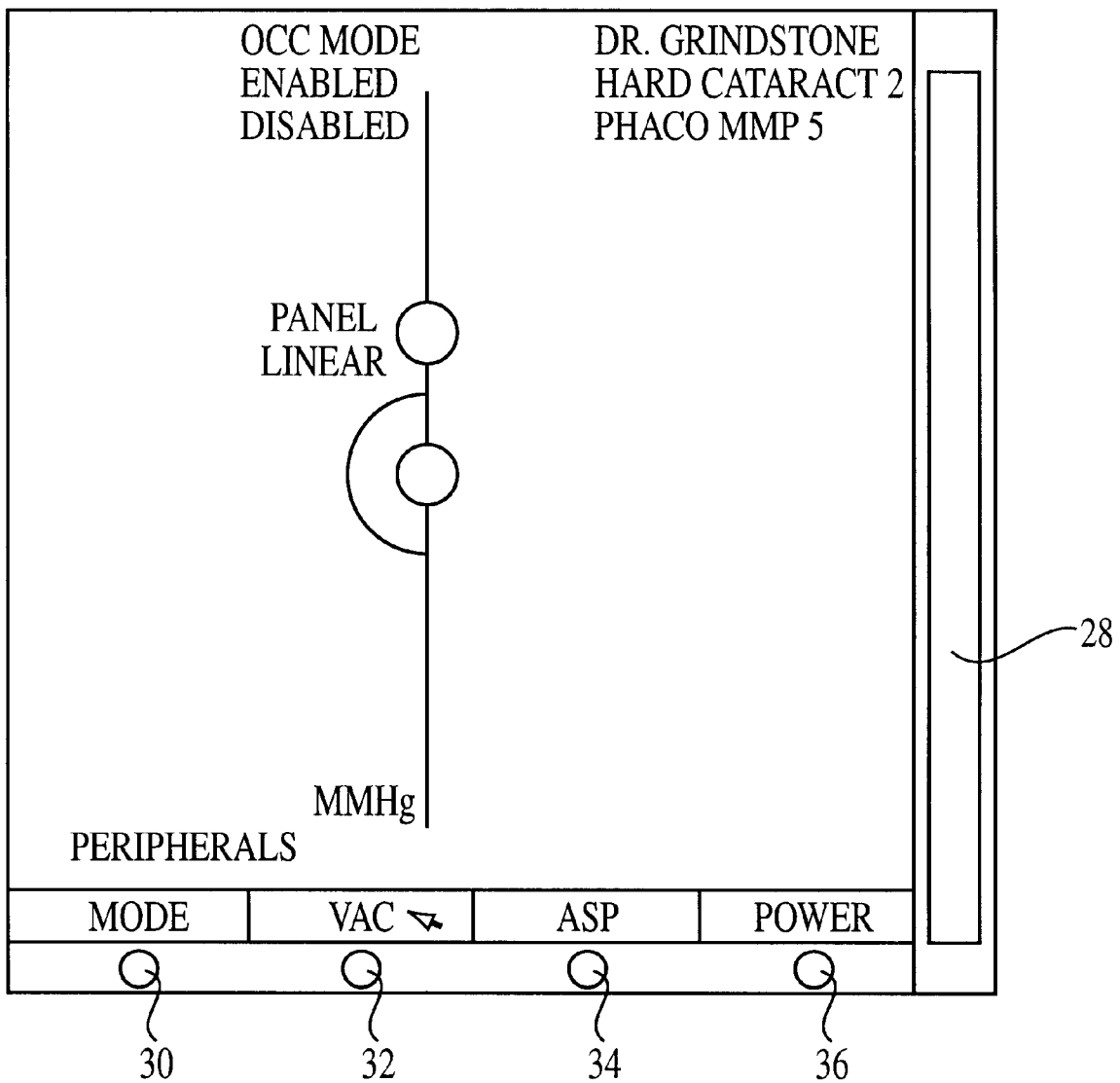

Turning now to FIG. 4, when the program button 32 is selected, a second vertical display 72 offers a selection of programs for saved preferences particularly associated with a plurality of users.

A new surgeon may be selected by movement of box 74 around the new surgeon listing by means on the slider switch 28 parallel to the vertical displays 72. Upon switching of the new surgeon a vertical display is now generated by the computer 56 shown in FIG. 5 in which an icon box 76 includes a space 80 for the entry of an alphabetical value and the sliding touch control means 48 is operative upon touching thereof to indicate possible alphabet letters for entry into the icon space 80 upon movement of the user's finger along the sliding switch when in contact therewith. Release of the sliding touch control means by the user's finger is effective for displaying a last possible alphabet character in the icon space and entry of such value into the computer 56.

Upon selection of a user indicated in FIG. 4 as Dr. Smith, the vertical display aligned with button 32 indicates all the various procedures and settings which are recorded for the Dr. Smith.

Upon selection of the program, for example, phaco for a specific doctor, vertical displays are generated and aligned with buttons 32, 34, 36 for vacuum, aspiration, and power setting respectively of the phacoemulsification handpiece. In addition, various status notices may also be provided as, for example, the notice in FIG. 7, the handpiece is not connected.

It should be appreciated that at any point during a surgical procedure, operating information may be changed. To change the information the user activates a menu by choosing one of the button switches 30, 32, 34, 36 and horizontally displayed information can be changed using the slider 48. The computer, through software, then changes the display by enlarging and brightening the active menu and dimming the other menus on the screen. See FIG. 8 in which the button 32 has activated the vertical display for vacuum settings.

As hereinabove noted, each of the boxes displayed in the vertical display may be moved by the slider switch 28 by movement of the contacting finger therewith. In addition, any of the icons requiring the value can have values entered by movement of a finger along the slider switch in a manner similar to that hereinbefore described with the entry of alphabetical figures into the icon box 76, see FIG. 5.

Figure 9:
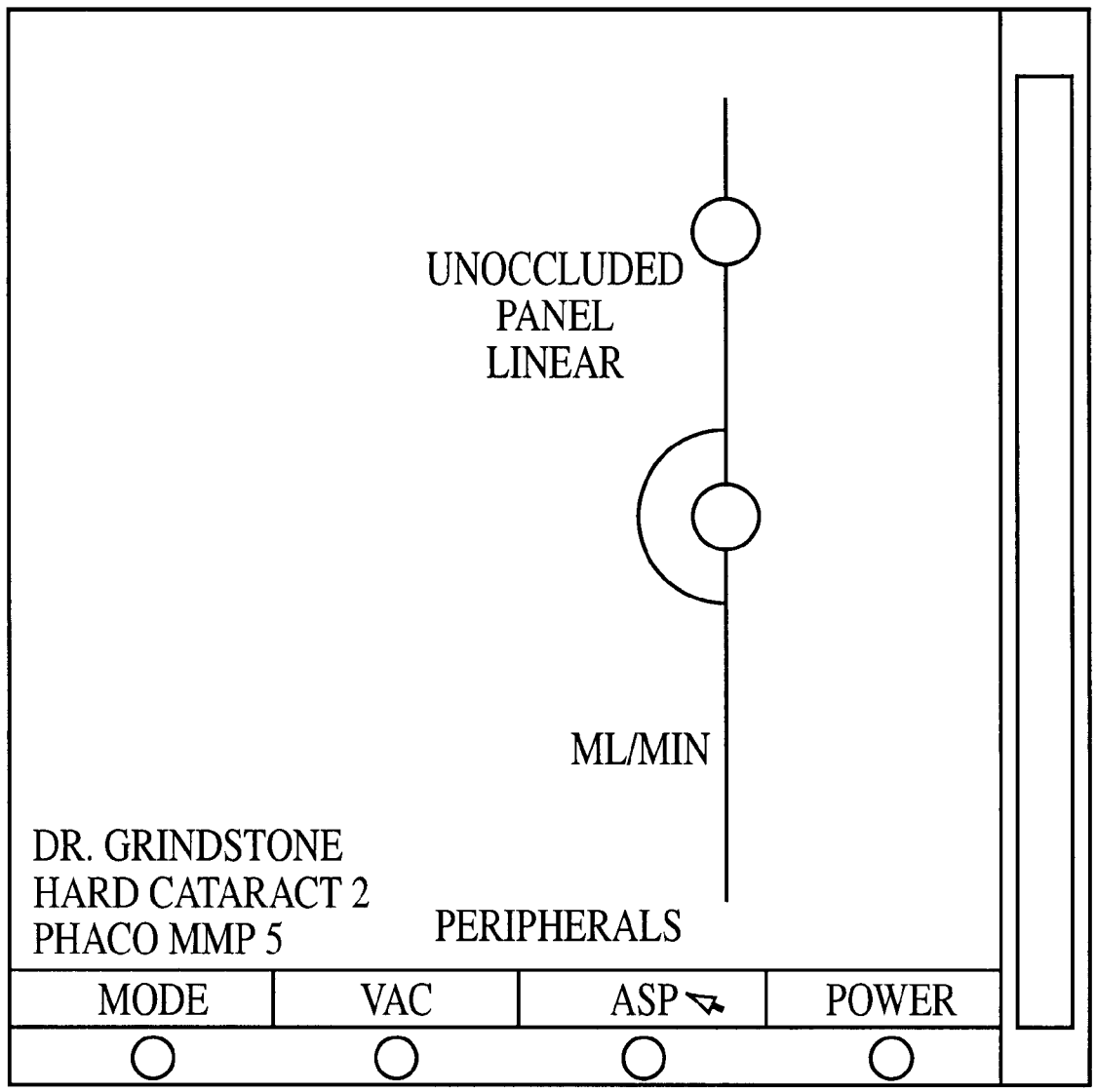
Figure 10:
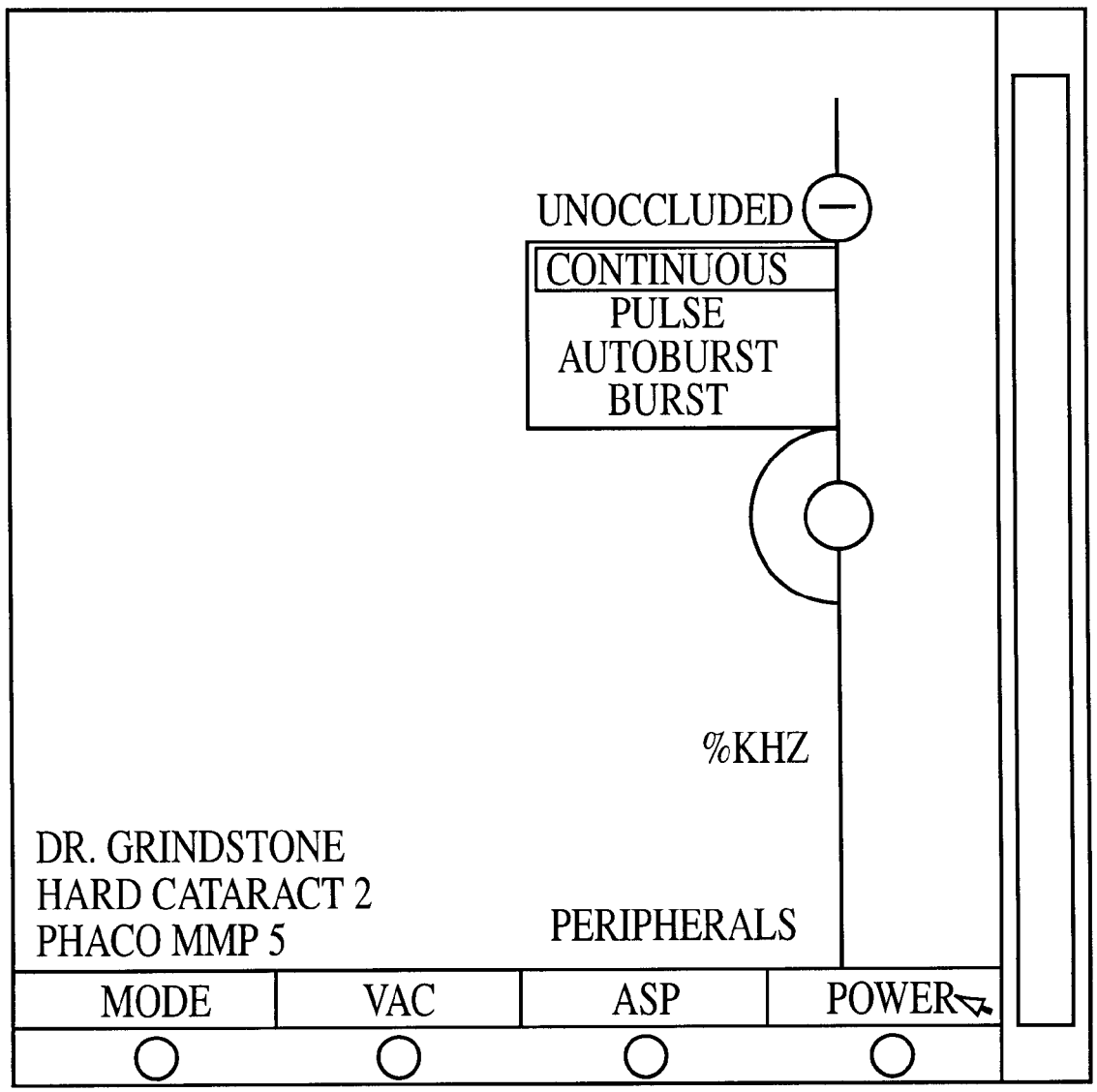
Figure 11:
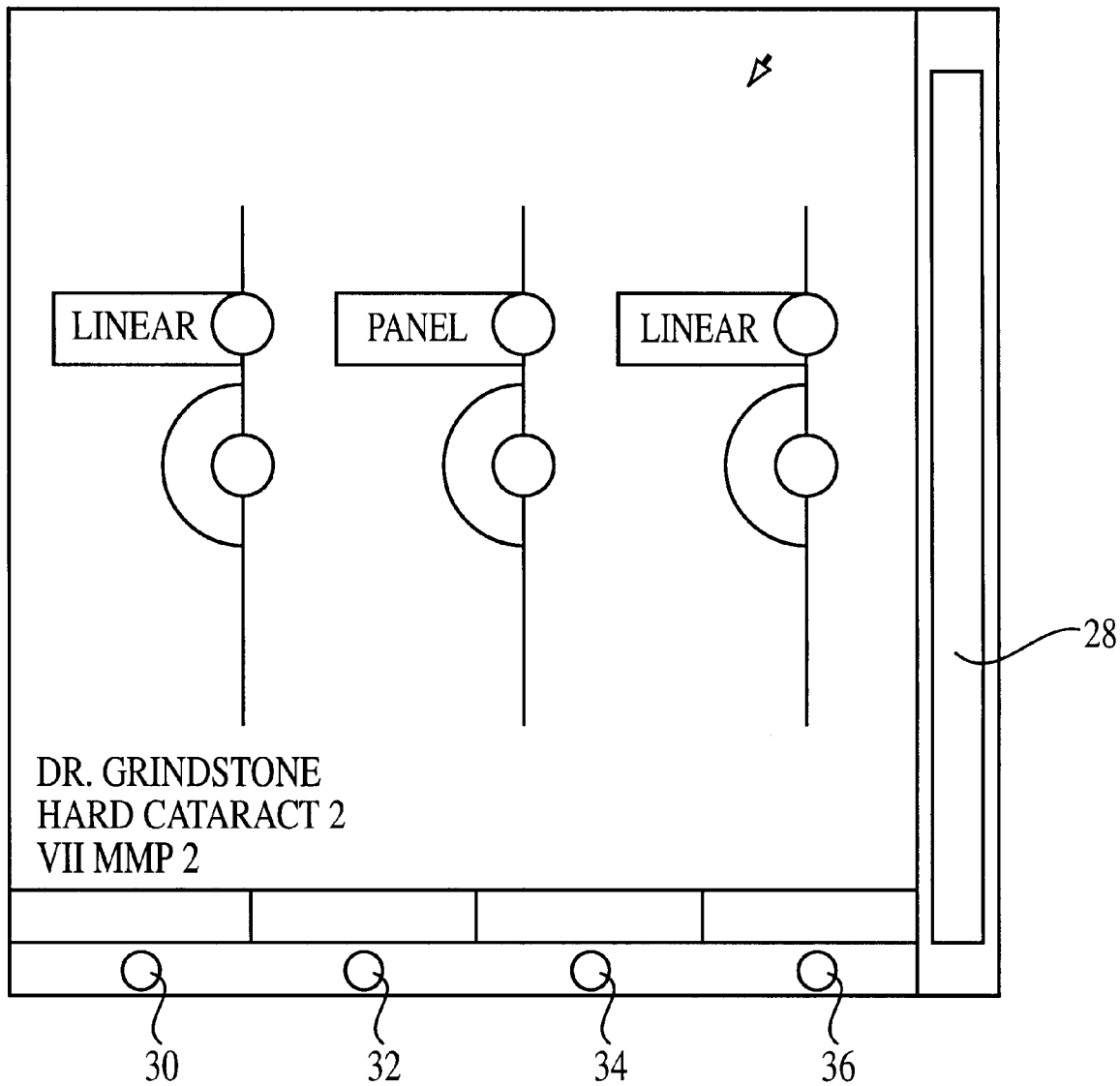

FIGS. 9 and 10 show the corresponding highlighted vertical displays for aspiration and power respectively for phaco operation. FIG. 11 shows vertical displays suitable for vitrectomy which includes vacuum settings, aspiration settings and cutting rates of the instruments.

Within the Program function all settings for a particular position and a specific procedure may be reviewed simultaneously on the screen as shown in FIG. 12.

Although there has been hereinabove described a specific arrangements of screen navigation control apparatus in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. Screen navigation control apparatus for an ophthalmic surgical instrument, the apparatus comprising:

a monitor having a screen;

a monitor bezel having a generally horizontal shelf aligned with a bottom of said screen and a generally vertical portion aligned with a side of said screen;

sliding touch control means, disposed in a continuous strip along a vertical portion of the bezel shelf, for selecting functions and alphanumeric data appearing in an activated vertical display; and a plurality of spaced apart switch means, disposed on the bezel horizontal portion, for activating corresponding vertical displays on said screen, each corresponding vertical display being aligned with one of the switch means;

means for generating said vertical displays generally parallel to said sliding touch control means, said vertical displays including a main menu having as a first vertical display a mode menu offering a selection of diathemy, phaco, irrigation/aspiration or vitrectomy mode of operating the surgical instrument, a second vertical display offering a selection of programs for saved preferences, a third vertical display offering a selection for diagnostics, fluidics, testing, setup and maintenance of the surgical instrument, and a fourth vertical display offering a selection for ending operation of the surgical instrument.

2. The apparatus according to claim 1 wherein said vertical displays include, upon selection of phaco mode of operating, a first selection display for vacuum settings, a second selection display for aspiration setting and a third selection display for power settings.

3. The apparatus according to claim 2 wherein the means for generating said vertical displays includes means for projecting a field of alphanumeric characters on said screen, spaced apart from said vertical displays, adjacent to sliding touch central means and parallel therewith, and highlighting a specific alphanumeric character corresponding to a position of a user's finger on the sliding touch control means.

4. The apparatus according to claim 3 wherein said sliding touch central means activates upon release of the control means.

5. The apparatus according to claim 4 wherein at least one of the vertical displays includes a list of readable options and a box outline and the sliding touch control means is operative upon touching thereof to move the box outline to surround one of the readable options, release of the sliding touch control means being effective to select the surrounded readable option and stabilize the box outline therearound.

6. The apparatus according to claim 4 wherein at least one of the vertical displays includes an icon having a space therein for entry of a numerical valve and the sliding touch control means is operative, upon touching thereof, to indicate possible numerical values for entry into the icon space upon movement of the user's finger along the sliding touch control means when in contact therewith, release of the sliding touch control means by the user's finger being effective to display a last possible numerical valve in the icon space.

7. The apparatus according to claim 5 wherein the at least one of the vertical displays includes an icon having a space therein for entry of a numerical valve and the sliding touch control means is operative, upon touching thereof, to indicate possible numerical values for entry into the icon space upon movement of the user's finger along the sliding touch control means when in contact therewith, release of the sliding touch control means by the user's finger being effective to display a last possible numerical valve in the icon space.

8. A screen navigation control method for an ophthalmic surgical instrument serviced by a console having a monitor having a screen for displaying operating functions and values, the method comprising the steps of:

providing a monitor bezel having a generally horizontal shelf aligned with a bottom of said screen and a generally vertical portion aligned with a side of said screen;

providing sliding touch control means, disposed in a continuous strip along the vertical portion of the bezel shelf, for selecting functions and alphanumeric data appearing in an activated horizontal display;

providing a plurality of spaced apart switch means, disposed on the bezel horizontal shelf, for activating corresponding vertical displays on said screen, each corresponding vertical display being aligned with one of the switch means;

providing means for generating said vertical displays generally parallel to said sliding touch control means, at least one of the vertical displays including a list of readable options and a box outline and the sliding touch control means is operative upon touching thereof to move the box outline to surround one of the readable options, release of the sliding touch control means being effective to select the surrounded readable option and stabilize the box outline therearound and at least one of the vertical displays including an icon having a space therein for entry of a numerical valve and the sliding touch control means is operative, upon touching thereof, to indicate possible numerical values for entry the icon space upon movement of the user's finger along the sliding touch control means when in contact therewith, release of the sliding touch control means by the user's finger being effective to display a last possible numerical value in the icon space.

\* \* \* \* \*